United States Patent
Wang et al.

(10) Patent No.: US 12,104,203 B2
(45) Date of Patent: Oct. 1, 2024

(54) METHOD FOR CONSTRUCTING LIBRARY OF CELL-FREE DNAS IN BODY FLUIDS AND APPLICATION THEREOF

(71) Applicant: BGI SHENZHEN, Shenzhen (CN)

(72) Inventors: Mingyue Wang, Shenzhen (CN); Longqi Liu, Shenzhen (CN); Chuanyu Liu, Shenzhen (CN); Liang Wu, Shenzhen (CN); Jiangshan Xu, Shenzhen (CN); Yue Yuan, Shenzhen (CN); Zhouchun Shang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 394 days.

(21) Appl. No.: 16/766,983

(22) PCT Filed: Nov. 27, 2017

(86) PCT No.: PCT/CN2017/113208
§ 371 (c)(1),
(2) Date: May 26, 2020

(87) PCT Pub. No.: WO2019/024341
PCT Pub. Date: Feb. 7, 2019

(65) Prior Publication Data
US 2021/0317516 A1 Oct. 14, 2021

(51) Int. Cl.
*C12Q 1/6855* (2018.01)
*C12N 15/10* (2006.01)
*C12Q 1/6806* (2018.01)

(52) U.S. Cl.
CPC .......... *C12Q 1/6855* (2013.01); *C12N 15/10* (2013.01); *C12N 15/1068* (2013.01); *C12Q 1/6806* (2013.01); *C12Q 2521/301* (2013.01); *C12Q 2525/155* (2013.01); *C12Q 2525/191* (2013.01); *C12Q 2525/307* (2013.01); *C12Q 2535/122* (2013.01)

(58) Field of Classification Search
CPC .............. C12Q 1/6806; C12Q 1/6855; C12Q 2525/155; C12Q 2525/191; C12Q 2535/122
See application file for complete search history.

(56) References Cited

U.S. PATENT DOCUMENTS

| | | | |
|---|---|---|---|
| 2010/0120098 A1* | 5/2010 | Grunenwald | C12N 15/10 435/193 |
| 2014/0274740 A1* | 9/2014 | Srinivasan | C12Q 1/6806 435/287.2 |
| 2017/0211143 A1 | 7/2017 | Shendure et al. | |
| 2018/0030532 A1* | 2/2018 | Jiang | C12Q 1/68 |

FOREIGN PATENT DOCUMENTS

| | | | | |
|---|---|---|---|---|
| CN | 102296065 A | | 12/2011 | |
| CN | 107083440 A | * | 8/2017 | ......... C12N 15/1013 |
| WO | 2010094040 A1 | | 8/2010 | |
| WO | 2014145078 A1 | | 9/2014 | |
| WO | 2015188192 A2 | | 12/2015 | |
| WO | 2016011414 A1 | | 1/2016 | |
| WO | WO-2016015058 A2 | * | 1/2016 | ........... C12Q 1/6869 |
| WO | WO-2017004083 A1 | * | 1/2017 | ......... C12N 15/1093 |

OTHER PUBLICATIONS

Marine et al. Applied and Environmental Microbiology 2011; 77: 8071-8079 (Year: 2011).*
Loewe et al. Methods 2013; 59: 126-131 (Year: 2013).*
Buenrostro, J.D., Wu, B., Chang, H.Y., and Greenleaf, W.J., 2015. "ATAC-seq: A Method for Assaying Chromatin Accessibility Genome-Wide." Curr. Protoc. Mol. Biol. 109:21.29.1-21.29.9. doi: 10.1002/0471142727.mb2129s109 (Year: 2015).*
Machine translation of Guo. Obtained Sep. 5, 2023. (Year: 2023).*
Search Report issued for for EP patent application 17920120.7 dated May 25, 2021.
Search Report issued for for EP patent application 17920120.7 dated Jan. 4, 2022.
Office Action issued for CN patent application Serial No. 201780097208.1, dated Feb. 23, 2023.

* cited by examiner

*Primary Examiner* — Angela M. Bertagna
*Assistant Examiner* — Francesca Filippa Giammona
(74) *Attorney, Agent, or Firm* — Z. Peter Sawicki; Westman, Champlin & Koehler, P.A.

(57) ABSTRACT

A method for constructing a library of cell-free DNAs in body fluids, comprising directly acting a transposase or an endonuclease on a body fluid sample, fragmenting the cell-free DNAs within, and performing amplification to obtain a library. Also provided is a test kit using the present method for prenatal diagnosis or early detection of cancer.

14 Claims, 5 Drawing Sheets
Specification includes a Sequence Listing.

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 1
ctgtctctta tacacatct                                                  19

<210> SEQ ID NO 2
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 2
tcgtcggcag cgtcagatgt gtataagaga cag                                  33

<210> SEQ ID NO 3
<211> LENGTH: 34
<212> TYPE: DNA
<213> ORGANISM: Artificial sequence
<220> FEATURE:
```

```
<223> OTHER INFORMATION: synthetic oligonucleotide

<400> SEQUENCE: 3
gtctcgtggg ctcggagatg tgtataagag acag                                  34

<210> SEQ ID NO 4
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 4
gccatgtcgt tctgtgagcc aagg                                             24

<210> SEQ ID NO 5
<211> LENGTH: 39
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: the first base is phosphorylated

<400> SEQUENCE: 5
gaacgacatg gctacgatcc gactttcgtc ggcagcgtc                             39

<210> SEQ ID NO 6
<211> LENGTH: 50
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (26)..(35)
<223> OTHER INFORMATION: n is a, c, g or t

<400> SEQUENCE: 6
tgtgagccaa ggagttgttg tcttcnnnnn nnnnngtctc gtgggctcgg                 50
```

METHOD FOR CONSTRUCTING LIBRARY OF CELL-FREE DNAS IN BODY FLUIDS AND APPLICATION THEREOF

CROSS-REFERENCE TO RELATED APPLICATIONS

This application is a US national phase application based upon PCT Application No. PCT/CN2017/113208, filed with the China National Intellectual Property Administration on Nov. 27, 2017, the entire content of which is incorporated herein by reference.

FIELD

The present disclosure relates to the field of sequencing technology, in particular to a method for constructing a library of cell-free DNAs in body fluid and its use in prenatal diagnosis and early detection of cancer.

BACKGROUND

French scientists Mandel and Mattes have firstly detected cell-free DNA fragments in human peripheral blood in 1948. These DNA fragments are mainly derived from fragmented chromatin of cleaved apoptotic or necrotic cells.

The research team of Lu Yuming from the Chinese University of Hong Kong has discovered that fetal cell-free DNAs are present in the peripheral blood of pregnant women in 1997, which opens the door for genetic detection of pregnant woman's peripheral blood. The technology for genetic detection of pregnant woman's peripheral blood is called non-invasive prenatal testing. Such a technology is performed according to the principle that since fetal DNAs are present in peripheral blood of pregnant women, cell-free DNAs in blood of pregnant women can be subjected to library construction and sequencing, further isolating fetal DNAs by comparing the single nucleotide polymorphism difference between maternal DNAs and fetal DNAs, such that prenatal diagnosis can be performed (Lo et al, Am. J. Hum. Genet 64, 218-224, 1999). At present, this technology is relatively mature in domestic and abroad, mainly for screening three common chromosomal diseases, respectively T21 chromosome abnormality (Down syndrome), T18 chromosome abnormality (Edward syndrome) and T13 chromosome abnormality (Patau's syndrome), with a detection accuracy rate up to 99% or above.

In addition, Lyon et al. determined that the cell-free DNA level in blood of cancer patients is associated with the metastasis of malignant tumors to a certain extent, which provides a theoretical basis for the non-invasive diagnosis of cancer. On this basis, early cancer detection technology is developed. With increased number of apoptosis and necrotic cells in the case of a pathological state of cancer, the cell-free DNAs that carry mutations specific to cancer cells are increasingly released into blood, thus the type of cancer and its development can be determined by testing the concentration or mutation status of cell-free DNAs in blood (Morelli et al., Ann Oncol 26, 731-736, 2015). Further, mutations of genes such as K-ras, EGFR and the like have been detected on the blood cell-free DNAs of cancer patients. These findings can be applied in the early diagnosis of malignant tumors such as lung cancer, breast cancer and the like.

It should be noted that the human body contains more than 400 cell types. Each of cell types has significant cell specificity on gene expression levels despite sharing one same genome, which is regulated by the cell-specific epigenome. Epigenomic information includes DNA methylation, histone modification, nucleosome localization and the like, and the cell source can be directly determined by the epigenomic information and an epigenome database reference. The newly research shows that cell-free DNAs in blood contain epigenomic information including methylation and nucleosome localization, which can be useful in tissue traceability.

Among them, the methylation of cell-free DNAs in blood can reflect the methylation of cells in source tissues to some extent, and the methylation level and location of different cell types of tissues are different, thus such a methylation can be useful in determining the cell type of cell-free DNAs. For example, Lo et al. reported a blood cell-free DNA methylation detection technique, that is, blood cell-free DNAs after treated with bisulfite are subjected to library construction and sequencing, and then methylation analysis, as such capable of being corresponded to specific cell types since the blood cell-free DNAs carry the methylation status of their source cells, thereby achieving tissue traceability (Lo et al., PNAS 112:5503-5512, 2015). This research can be useful in a variety of diagnoses, including prenatal diagnosis, cancer localization and metastasis diagnosis of tumor cells, immune system rejection diagnosis of organ-transplanted patients and the like. However, this blood cell-free DNA methylation detection technique still has some disadvantages. For example, 1) a small number of methylation sites on genome and low concentration of blood cell-free DNAs results in poor accuracy on detection results, and 2) complex steps for methylation sequencing may generate a risk of losing a large amount of DNA methylation information, resulting in low sequencing quality, serious noise and the like.

Further, nucleosome localization information in cells can be useful in distinguishing cell and tissue types. A large number of documents reported that the length of blood cell-free DNA is concentrated around 167 bp, which is consistent with the length of nucleosome DNA, indicating that plenty of blood cell-free DNAs are DNAs comprised in nucleosomes. In 2016, Jay Shendure et al. constructed a sequencing library after extracting cell-free DNAs from blood, and then positioned the nucleosome information of blood cell-free DNAs to different cell types through deep sequencing strategy, thus realizing tissue traceability (Shendure et al., CELL 164, 57-68 (2016); Speicher et al., Nature Genetics 48, 1273-1278 (2016)). However, this method includes directly extracting the blood cell-free DNAs to construct a library, and then analyzing the nucleosome localization through the sequencing data, while the naked DNAs presented in blood will generate noise and interfere with the normal nucleosome DNA localization, which results in poor efficiency of tissue traceability. Moreover, this method utilizes a deep sequencing strategy, which makes a relatively high sequencing cost, thus being difficult to form a wide range of applications in commercialization.

Besides, there are studies on chromatin accessibility sequencing technology specifically for accessible chromatin regions, comprising cell lysis and Tn5 transposase treatment thus inserting a sequencing adapter into the accessible chromatin regions, amplification of all accessible chromatin regions via a PCR amplification method, library construction and sequencing (Chang et al., Curr. Protoc. Mol. Biol.109:21.29.1-21.29.9). However, this technique exactly excludes the nucleosome DNA information, thus cannot be useful in tissue traceability through nucleosome DNAs as well.

In summary, the current methods for non-invasive prenatal testing and early detection of cancer are conducted by first extracting blood cell-free DNAs and then routinely constructing a library, however, existing the following problems. For example, 1) blood cell-free DNAs are in a low content, which is easily to cause DNA loss during the library construction, resulting in failure of library construction or low detection sensitivity. Further, 2) for the existing library construction methods, cell-free DNAs in blood are firstly extracted, followed by library construction and sequencing on the extracted cell-free DNAs, thus only the sequence or methylation information of blood cell-free DNAs can be obtained finally, while the distribution information of nucleosome may be lost during the library construction. Further, 3) the cost for sequencing is too expensive. Therefore, there is an urgent need to develop an efficient and sensitive method for constructing a library of blood cell-free DNAs, which is also capable of screening out nucleosome fragments from the blood cell-free DNAs for tissue traceability.

SUMMARY

In view of the defects as mentioned above in the prior art, the present disclosure aims to provide a method for constructing a library of cell-free DNAs in body fluid and its use in prenatal diagnosis and early detection of cancer. In the present disclosure, a body fluid sample is directly treated with an enzyme such that the cell-free DNAs in the body fluid sample are fragmented and added with an adapter, without extraction of cell-free DNAs from the body fluid sample. For the present method, steps are simple, cost for library construction is cheap, library construction can be based on trace amount of cell-free DNAs in body fluid, and cell-free nucleosome DNA information in body fluid is retained maximally during library construction.

The present disclosure achieves the objectives as described above according to the following technical solutions.

In one aspect, provided in the present disclosure is a method for constructing a library of cell-free DNAs in a body fluid sample, comprising steps of
1) directly treating the body fluid sample by an enzyme, such that the cell-free DNAs in the body fluid sample are fragmented under the enzyme, and
2) amplifying the fragmented DNAs obtained in step 1) to obtain the library of cell-free DNAs in the body fluid sample.

In a preferred and specific embodiment, the body fluid sample is at least one selected from blood, urine and saliva. In the body fluid sample, two types of cell-free DNAs are existed, including nucleosome DNAs bound to histone and unbound and naked DNAs. After the treatment of enzyme, naked DNAs are cut into fragments of about 50 bp, and the nucleosome DNAs may be cut into fragments above 50 bp due to binding to histones.

In a preferred embodiment, the enzyme is a transposase or an endonuclease. Preferably, the transposase is Tn5 transposase and the endonuclease is MNase or DNase.

It should be noted that the body fluid sample can be treated by either of transposase and endonuclease. In embodiments of using transposase, the cell-free DNAs in the body fluid sample can be not only fragmented but also added with an adapter. In embodiments of using endonuclease, the cell-free DNAs in the body fluid sample can just be fragmented, and the addition of adapter needs to be performed in a subsequent individual step.

In a preferred and specific embodiment, the step 1) comprises utilizing a transposase to treat the body fluid sample containing the cell-free DNAs, such that the cell-free DNAs are fragmented and added with an adapter through a transposition reaction mediated by the transposase, thereby obtaining DNA fragments containing adapter sequences; preferably, the step 1) further comprises extracting the DNA fragments containing adapter sequences in the body fluid sample.

In a further preferred embodiment, the adapter for the transposition reaction is an adapter mixture prepared by steps of:
a) annealing a primer A of 5'-CTGTCTCTTATACA-CATCT-3'(SEQ ID NO: 1) and a primer B of 5'-TCGTCGGCAGCGTCAGATGTGTATAAGA-GACAG-3'(SEQ ID NO: 2) to obtain a first adapter,
b) annealing a primer A of 5'-CTGTCTCTTATACA-CATCT-3' (SEQ ID NO: 1) and a primer C of 5'-GTCTCGTGGGCTCGGAGATGTGTATAAGA-GACAG-3'(SEQ ID NO: 3) to obtain a second adapter, and
c) mixing the first adapter and the second adapter to obtain the adapter mixture.

Preferably, the adapter mixture is embedded with the transposase to obtain a transposase-embedding complex for the transposition reaction.

Preferably, the adapter mixture is embedded with the Tagment Enzyme Advanced V5S containing transposase.

Preferably, a volume ratio of the adapter mixture to the Tagment Enzyme Advanced V5S is 1:20 to 1:25 preferably 1:24.5.

Preferably, the embedding is performed at 22 to 28° C. preferably 25° C. for 40 to 80 minutes preferably 60 minutes.

In specific embodiments, preferably, the transposition reaction is conducted by incubating the transposase-embedding complex and the body fluid sample at a condition suitable for transposition reaction.

Preferably, the volume ratio of the transposase-embedding complex to the body fluid sample for transposition reaction is 1:50 to 1:80 preferably 1:62.5.

Preferably, the temperature for transposition reaction is 35 to 40° C. preferably 37° C.

Preferably, the time period for transposition reaction is 55 to 65 minutes preferably 60 minutes.

In a specific embodiment of the transposition reaction, the used Tn5 transposase is capable of cleaving DNAs randomly, such that the naked cell-free DNAs (i.e. cell-free DNAs not wrapped around histones) in plasma would be cut into fragments of about 50 bp by the Tn5 transposase, while the nucleosome DNAs (i.e. cell-free DNAs wrapped around histones) in plasma would be cut into fragments above 50 bp by the Tn5 transposase. DNA fragments having different lengths can be distinguished through PE50+10 sequencing and the like, which is for subsequent screening of nucleosome DNA sequences, and further analysis of epigenetic information of DNA sequences and the enrichment of DNA sequences in regulating region and transcription initiation region such as promoter or enhancer and the like regions of different genes. Subsequently, the nucleosome DNA sequences obtained from library construction can be used to realize the tissue traceability of cell-free DNAs in blood according to the epigenomic information.

In another preferred embodiment, the step 1) comprises utilizing an endonuclease to treat the body fluid sample containing the cell-free DNAs, such that the cell-free DNAs are fragmented by the endonuclease, and adding an adapter at both ends of the fragmented DNAs, thereby obtaining DNA fragments containing adapter sequences;

preferably, the step 1) further comprises extracting the fragmented DNAs in the body fluid sample after the fragmentation reaction.

In a preferred and specific embodiment, the amplification in step 2) comprises two amplification processes.

Preferably, the cycle number N to be used in a second amplification process is determined by the qPCR reaction after a first amplification process.

In a preferred and specific embodiment, the method further comprises a step of 3) subjecting the library of cell-free DNAs in the body fluid sample obtained in step 2) to cyclization and enzyme digestion.

Preferably, the cyclization comprises denaturing the double-stranded DNAs in the library of cell-free DNAs in the body fluid sample into single-stranded DNAs, and ligating the single-stranded DNAs with an oligonucleotide fragment complementary to a partial region of the single-stranded DNA through base-complementary pairing.

Preferably, the single-stranded DNAs are cyclized by using the oligonucleotide fragment (i.e., a mediator) of 5'-GCCATGTCGTTCTGTGAGCCAAGG-3' (SEQ ID NO: 4).

Preferably, the enzyme digestion is performed by using exonuclease I and exonuclease III to remove non-cyclized DNAs.

Preferably, the step 3) further comprises purifying the enzyme-digested library, preferably using magnetic beads for purification.

In a second aspect, provided in the present disclosure is a method for obtaining epigenetic information of an individual, comprising steps of 1) obtaining a library of cell-free DNAs in a body fluid sample of an individual according to the method of the first aspect, and 2) sequencing and analyzing the library of cell-free DNAs in the body fluid sample obtained in step 1) to obtain epigenetic information of the individual.

In a third aspect, provided in the present disclosure is use of the method for constructing a library of cell-free DNAs in a body fluid sample as described in the first aspect or the method for obtaining epigenetic information of an individual as described in the second aspect in prenatal diagnosis and early detection of cancer.

In a fourth aspect, provided in the present disclosure is a method for prenatal diagnosis or early detection of cancer, comprising performing the method for constructing a library of cell-free DNAs in a body fluid sample as described in the first aspect or the method for obtaining epigenetic information of an individual as described in the second aspect.

In a fifth aspect, provided in the present disclosure is a kit for prenatal diagnosis or early detection of cancer through analysis of cell-free DNAs in a body fluid sample, comprising reagents, primers, a mediator or any combination thereof as used in the method as described in the first aspect.

Preferably, the kit comprises one or more selected from: Tn5 transposase, MNase or Dnase, a primer A of 5'-CTGTCTCTTATACACATCT-3' (SEQ ID NO: 1), a primer B of 5'-TCGTCGGCAGCGTCA-GATGTGTATAAGAGACAG-3' (SEQ ID NO: 2) and a primer C of 5'-GTCTCGTGGGCTCG-GAGATGTGTATAAGAGACAG-3' (SEQ ID NO: 3), the mediator of 5'-GCCATGTCGTTCTGTGAGC-CAAGG-3' (SEQ ID NO: 4), and enzymes and/or reagents for transposition reaction, PCR amplification, enzyme digestion and ligation reaction.

Advantages of the Present Disclosure Over the Prior Art

As mentioned above, the methods in the prior art usually include first extracting cell-free DNAs from a body fluid sample, followed by fragmenting via Tn5 transposase and library construction, however, existing disadvantages of poor accuracy on traceability results, requirement of deep sequencing, expensive cost and the like.

In the present disclosure, a body fluid sample is directly treated with an enzyme (such as a transposase or an endonuclease), such that the cell-free DNAs in the body fluid sample are fragmented and added with an adapter, thus achieving library construction directly on the cell-free DNAs in the body fluid sample. According to the method of the present disclosure, the steps are simple, the cost for library construction is cheap, and the gene information lost during the sequencing is reduced, thus maximally retaining cell-free DNA information in body fluid, especially the nucleosome DNA information. Thus, the present method for constructing a library of cell-free DNAs in body fluid is capable of not only achieving library construction based on minute amount of cell-free DNAs in body fluid, but also obtaining epigenetic information of cell-free DNAs in body fluid. Further, tissue traceability can be realized through deep analysis of the obtained epigenetic information, especially the nucleosome DNA information.

The method provided in the present disclosure proposed a new research method for studying the cell-free DNAs in body fluid, which has good prospects in clinical applications such as prenatal diagnosis, early detection of tumor, new disease surveillance and the like.

DETAILED DESCRIPTION

In order to facilitate understanding the present disclosure, the present examples herein are specified as below. Those skilled in the art should understand that the described examples are merely to promote understanding of the present disclosure, which should not be considered as a specific limitation to the present disclosure.

Example 1 Library Construction of Cell-Free DNAs in Peripheral Blood and Analysis of Epigenetic Information This example includes a series of steps including plasma sample preparation, direct transposition of the plasma sample by Tn5 transposase, DNA amplification after transposition, Tn5 library construction, PE50+10 sequencing, screening nucleosome fragments and the like. Tn5 transposase was prepared according to the instructions of TruePrep Mini DNA Sample Prep Kit from Vazyme Company.

1.1 Plasma Sample Preparation 1.1.1 Plasma Sample Collection 10 mL of whole blood samples from healthy human were collected, centrifuged at 1600 g and 4° C. for 10 minutes, and the supernatant (i.e. plasma) was collected into a 15 mL new centrifuge tube.

1.1.2 Plasma Purification

Plasma purification was conducted according to either of the following methods (Methods I and II).

1.1.2.1 Method I—Filtration by Filter Head 3 mL plasma was filtered by a 10 mL syringe equipped with 0.2 m filter head and transferred into a new eppendorf (EP) tube, with 0.5 mL plasma lost.

1.1.2.2 Method II—Twice Centrifugation Method

The plasma was centrifuged again at 16000 g and 4° C. for 10 minutes, and the supernatant was collected into a 15 mL new centrifuge tube.

1.2 Transposition of Partial Plasma

Partial plasma was subjected to the transposition reaction according to the present method, in which the plasma was directly used for transposition reaction.

1.2.1 Preparation of Adapter Mix 1.2.1.1 Reference Primers and Sequences Thereof are:

a primer A of
(SEQ ID NO: 1)
5'-CTGTCTCTTATACACATCT-3', a primer B of
(SEQ ID NO: 2)
5'-TCGTCGGCAGCGTCAGATGTGTATAAGAGACAG-3',
and a primer C of
(SEQ ID NO: 3)
5'-GTCTCGTGGGCTCGGAGATGTGTATAAGAGACAG-3'.

1.2.1.2 The primer A, primer B and primer C were dissolved to 100 μM by an annealing buffer.

1.2.1.3 The following reaction systems were prepared, referring to Table 1.

TABLE 1

Preparation of Adapter Mix reaction systems

| Annealing reaction 1 | | Annealing reaction 2 | |
|---|---|---|---|
| primer A (100 μM) | 10 μL | primer A (100 μM) | 10 μL |
| primer B (100 μM) | 10 μL | primer C (100 μM) | 10 μL |
| Total volume | 20 μL | Total volume | 20 μL |

1.2.1.4 A first annealing product (i.e. a first adapter) and a second annealing product (i.e. a second adapter) were respectively vortexed to thoroughly mix and centrifuged briefly to make the solution back the tube bottom, after that the tubes were placed in a PCR instrument and subjected to the following reaction procedures: 75° C. for 15 minutes; 60° C. for 10 minutes; 50° C. for 10 minutes; 40° C. for 10 minutes; and 25° C. for 30 minutes.

1.2.1.5 After the completion of reaction, the first annealing product and the second annealing product in a same volume were mixed uniformly. The obtained mixture is named as Adapter Mix, stored at −20° C.

1.2.2 The Adapter Mix was embedded with the Tn5 transposase to obtain a transposase-embedding complex.

1.2.2.1 The following reaction components in Table 2 were respectively added into a sterilized PCR tube. In Table 2, the Tagment Enzyme Advanced V5S is BGI V5S reagent containing 1000U Tn5 transposase (Supplier: BGI, Catalog Number: BGE005S).

TABLE 2

Embedding system of Adapter Mix and Tn5 transposase

| Reagent | Volume (μL) |
|---|---|
| Tagment Enzyme Advanced V5S | 98 |
| Adapter Mix | 4 |
| Coupling Buffer V5S | 98 |
| Total volume | 200 |

1.2.2.2 The mixture in the tube was gently pipetted by a pipettor to thoroughly mix.

1.2.2.3 The mixture in the tube was reacted at 25° C. for 60 minutes. The reaction product is named as the Tagment Enzyme Advanced Mix V5S, stored at −20° C.

1.2.3 Fragmentation of Blood Cell-Free DNAs

A plasma transposition reaction system was prepared, referring to Table 3. The mixture was uniformly mixed after prepared on ice, and then subjected to the transposition reaction at 37° C. on a constant temperature metal mixer for 60 minutes.

TABLE 3

Plasma transposition reaction system

| Reagent | Volume (μL) |
|---|---|
| plasma | 500 |
| 5×TAG buffer | 140 |
| Tagment Enzyme Advanced Mix V5S | 10 |
| PBS | 50 |
| Total volume | 700 |

1.3 Extraction of Plasma Cell-Free DNAs after Transposition Reaction 1.3.1 The plasma cell-free DNAs after transposition reaction were extracted by using Magen blood cell-free DNA extraction kit (MAGEN MD5432-01).

1.3.2 After the transposition reaction, 25 μL proteinase K and 35 μL MagBind magnetic beads were added to a 1.5 mL new centrifuge tube.

1.3.3 The plasma transposition reaction system after transposition reaction obtained in 1.2.3 were transferred to the tube containing proteinase K in 1.3.2 and then shaken for 5 seconds.

1.3.4 700 μL of buffer MLE was added to the mixture in 1.3.3 and vortexed to mix, followed by incubated with shaking at 55° C. for 15 minutes.

1.3.5 The tube in 1.3.4 was transferred to a magnetic separator, and stilled for 5 to 10 minutes for adsorption of magnetic beads.

1.3.6 The solution in tube was carefully aspirated and discarded.

1.3.7 320 μL of buffer MW1 was added into the tube, and vortexed to mix for 15 seconds.

1.3.8 The tube in 1.3.7 was transferred to the magnetic separator, stilled for 3 to 5 minutes to adsorb magnetic beads, followed by aspirating the solution and discarded.

1.3.9 320 μL of buffer MW2 was added into the tube, and vortexed to mix for 15 seconds.

1.3.10 The tube in 1.3.9 was transferred to the magnetic separator, stilled for 3 to 5 minutes to adsorb magnetic beads, followed by aspirating the solution and discarded.

1.3.11 Steps 1.3.9 and 1.3.10 were repeated.

1.3.12 The tube was centrifuged briefly to concentrate the droplets on the tube wall, and then transferred to the magnetic separator, aspirating the solution and discarded.

1.3.13 The tube was dried in air for 5 to 10 minutes.

1.3.14 20 µL of buffer AE was added and pipetted to mix.

1.3.15 The tube was stilled at room temperature for 3 minutes.

1.3.16 The tube was transferred to the magnetic separator, stilled for 3 minutes to dissolve DNAs.

1.3.17 The DNA solution was transferred to a 1.5 mL new centrifuge tube.

1.3.18 The DNA concentration was detected by using the Qubit device.

1.4 Amplification of Fragmented DNAs 1.4.1 A PCR reaction system was prepared in a 0.2 mL PCR tube according to Table 4.

TABLE 4

First amplification reaction system of transposition product

| Reagent | Volume (µL) |
| --- | --- |
| DNA solution | 18 |
| NEBNext High-Fidelity 2xPCR Master Mix | 25 |
| N5 primer (25 µM) | 2.5 |
| N7 primer (25 µM) | 0.7 |
| Total volume | 20 |

*Note:
the DNA solution for Example 1 is the purified DNA solution obtained in step 1.3.17, and the DNA solution for the following Comparative Example 1 is the purified DNA solution obtained in step 2.4.
N5 primer:
Pho-GAACGACATGGCTACGATCCGACTTTCGTCGGCAGCGTC
(SEQ ID NO: 5).
N7 primer:
TGTGAGCCAAGGAGTTGTTGTCTTCNNNNNNNNNNGTCTCGTGGGCTCGG
(SEQ ID NO: 6), in which, NNNNNNNNNN represents a label sequence consisting of 10 random bases, and the label sequence for each sample is different.

1.4.2 The first amplification process was conducted according to the following parameters:

| 1 cycle | 5 minutes | 72° C. |
| --- | --- | --- |
| | 30 seconds | 98° C. |
| 8 cycles | 10 seconds | 98° C. |
| | 30 seconds | 63° C. |
| 1 cycle | 1 minute | 72° C. |
| | holding | 4° C. |

1.5 Q-PCR Determination and Second Amplification 1.5.1 Preparation of Q-PCR Reaction System (as Shown in Table 5)

TABLE 5 qPCR reaction system for determination of cycle number to be used in the second amplification

| Reagent | Volume (µL) |
| --- | --- |
| DNA solution | 4 |
| 2×SYBR ® Premix Ex Taq ™ II | 10 |
| Primer B (20 µM) | 0.5 |
| Primer C (20 µM) | 0.5 |
| ROX | 0.08 |
| NF-H$_2$O | 4.92 |
| Total volume | 20 |

1.5.2 qPCR reaction was conducted according to the following parameters:

| 1 cycle | 30 seconds | 98° C. |
| --- | --- | --- |
| 40 cycles | 10 seconds | 98° C. |
| | 30 seconds | 63° C. |
| | 1 minute | 72° C. |

Figure 1:
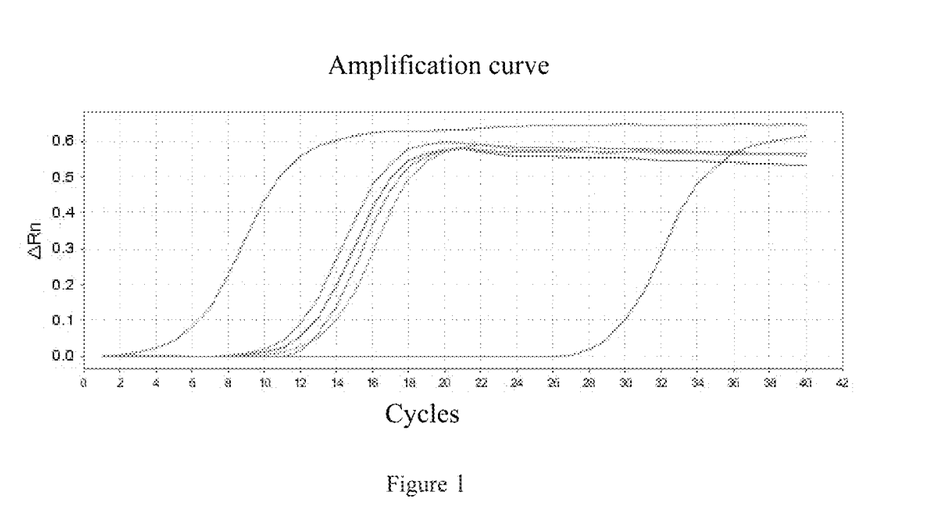
FIG. 1 is a graph showing data of cycle number at plateau phase determined by qPCR reaction in Example 1.

As shown in FIG. 1, the cycle number corresponding to ⅓ of fluorescence intensity at plateau phase in the Rn/Cycle curve of qPCR linear amplification is the cycle number N to be used in the second amplification.

1.5.3 The second amplification process was conducted according to the following parameters:

| 1 cycle | 5 minutes | 72° C. |
| --- | --- | --- |
| | 30 seconds | 98° C. |
| N cycles | 10 seconds | 98° C. |
| | 30 seconds | 63° C. |
| | 1 minute | 72° C. |
| 1 cycle | 5 minutes | 72° C. |
| | holding | 4° C. |

Figure 2:
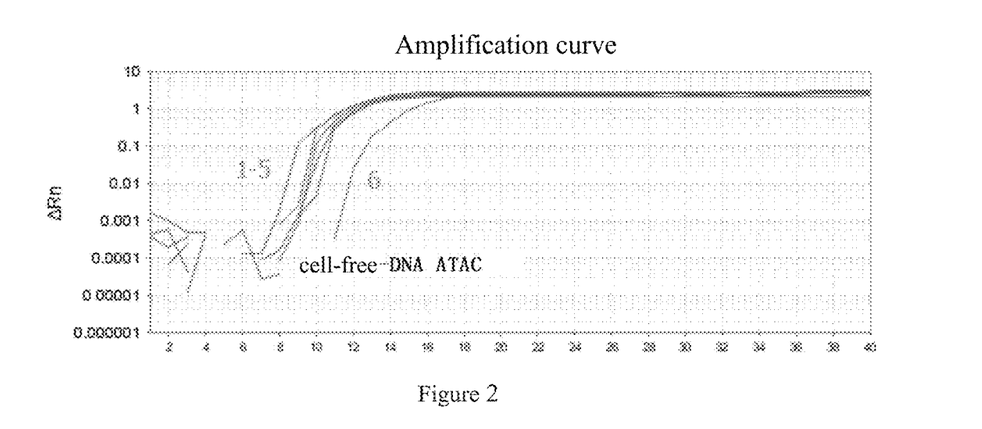
FIG. 2 is a graph showing sample amplification curves in Example 1.

In which, N is the cycle number determined in step 1.5.2. The sample amplification curves are shown in FIG. 2.

1.6 Double Size Selection by XP Magnetic Beads 1.6.1 The volume of PCR tube was checked and made up to 50 µL with NF—H$_2$O.

1.6.2 40 µL magnetic beads (0.8×) were added to the PCR tube, mixed by pipetting and stilled at room temperature for 5 minutes.

1.6.3 The PCR tube was placed on the magnetic separator for 2 minutes, and the supernatant was transferred to a new PCR tube, in which DNA fragments in the supernatant have a length less than 350 bp.

1.6.4 35 µL magnetic beads (0.7×) were added, mixed uniformly and stilled at room temperature for 5 minutes.

1.6.5 The PCR tube was placed on the magnetic separator for 2 minutes, and the supernatant containing small DNA fragments and RNAs was removed.

1.6.6 The PCR tube was kept on the magnetic separator, and 150 µL of pre-cooled 80% ethanol was added to wash twice (30 seconds).

1.6.7 The PCR tube was kept on the magnetic separator for 5 minutes to allow water evaporate.

1.6.8 20 µL TE Buffer (AMBION AM9858) was added to elute DNAs, gently mixed by pipetting and incubated at room temperature for 5 minutes.

1.6.9 The PCR tube was kept on the magnetic separator for 2 minutes, and the supernatant was transferred to a new PCR tube carefully, avoiding aspirating any magnetic beads.

1.6.10 Qubit dsDNA High sensitivity assay kit (INVITROGEN Q32854) was used for DNA quantification.

Figure 3:
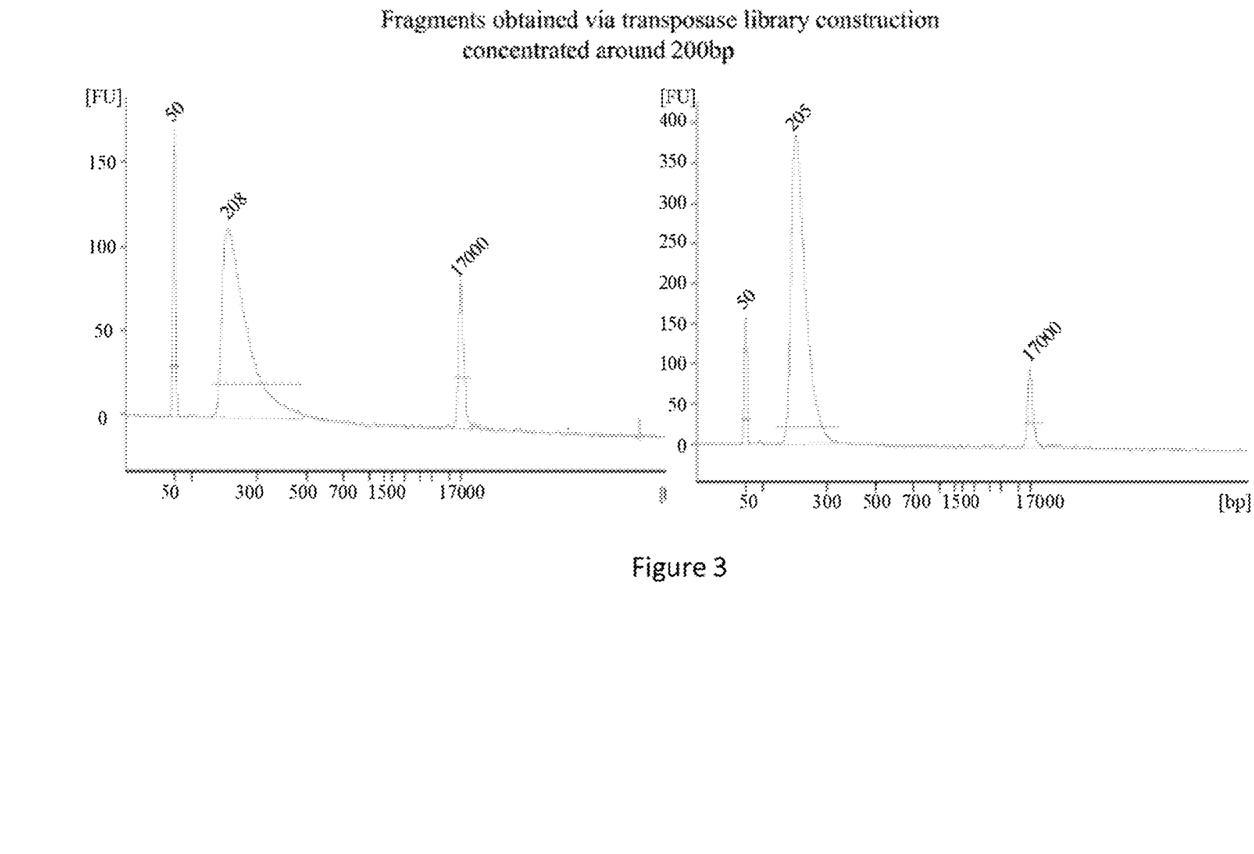
FIG. 3 is a graph showing Agilent 2100 detection results of part samples after double size selection by magnetic beads in Example 1.

1.6.11 The resulting DNA was tested by using Agilent 2100, and the results are shown in FIG. 3.

1.7 Library cyclization and enzyme digestion 1.7.1 The single-stranded mediator of 5'-GC-CATGTCGTTCTGTGAGCCAAGG-3' (SEQ ID NO: 4) was used.

1.7.2 324.5 ng of the purified DNAs obtained in step 1.6 was mixed with 5 μL single-stranded mediator (20 μM), and was made up to 70 μL volume with sterile ultrapure water.

1.7.3 The tube containing the DNA mixture obtained in step 1.7.2 was transferred to a thermal cycler, reacted at 95° C. for 3 minutes, and then quickly placed on ice for 10 minutes.

1.7.4 The single-stranded DNA ligation reaction system was prepared according to Table 6, mixed uniformly and then quickly centrifuged for 3 seconds.

TABLE 6

Single-stranded DNA ligation reaction system

| Reagent | Volume (μL) |
|---|---|
| DNA mixture | 70 |
| 10×TA buffer | 12 |
| 100 mM ATP | 1.2 |
| T4 DNA ligase (600 U/μL) | 0.42 |
| NF-H$_2$O | 36.38 |
| Total volume | 120 |

* Note:
DNA mixture in Table 6 is the solution obtained in step 1.7.3.

1.7.5 The single-stranded DNA ligation reaction system obtained in step 1.7.4 was transferred to a thermal cycler, reacted at 37° C. for 60 minutes, and temporarily stored at 4° C.

1.7.6 The enzyme digestion reaction system was prepared according to Table 7, mixed uniformly, and quickly centrifuged for 3 seconds.

TABLE 7

Single-stranded DNA enzyme digestion reaction system

| Reagent | Volume (μL) |
|---|---|
| DNA ligation mixture | 120 |
| 10×TA buffer | 0.8 |
| EXO I (20 U/μL) | 3.9 |
| EXO III (100 U/μL) | 1.3 |
| F-H$_2$O | 2 |
| Total volume | 128 |

* Note:
EXO I is exonuclease I and EXO III is exonuclease III in Table 7.

1.7.7 The enzyme digestion reaction system obtained in step 1.7.6 was transferred to a thermal cycler, reacted at 37° C. for 30 minutes, and temporarily stored at 4° C.

1.8 Library Collection 1.8.1 After vortexed to mix, 170 μL of PEG32 magnetic beads were added into 128 L of PCR product obtained in step 1.7, gently pipetted for 10 times by a pipettor to thoroughly mix, and then incubated at room temperature for 10 minutes.

1.8.2 The EP tube was briefly centrifuged and placed on the magnetic separator to separate magnetic beads and solution, stilled for 5 minutes to clear the solution which was carefully removed.

1.8.3 200 μL of freshly prepared 80% ethanol was added to the EP tube kept staying on the magnetic separator for rinsing the magnetic beads, and the supernatant was carefully removed after incubating at room temperature for 30 seconds.

1.8.4 The step 1.8.3 was repeated, in total of twice rinse by 80% ethanol.

1.8.5 The EP tube was kept staying on the magnetic separator, and the lip was opened to dry in air for 10 minutes.

1.8.6 The EP tube was taken out from the magnetic separator, and 25 μL of sterile ultrapure water was added to elute DNAs, followed by gently pipetting by a pipettor to thoroughly mix. After stilled at room temperature for 5 minutes, the EP tube was briefly centrifuged and placed on the magnetic separator to separate the magnetic beads and solution. After cleared (about 5 minutes), the supernatant was carefully drawn into a new EP tube and store at −20° C.

1.8.7 1 μL of purified product was detected for ssDNA concentration.

1.9 Sequencing by a Sequencer 6 ng of constructed library obtained in step 1.8 was used to prepare DNA nanoballs (DNBs) through Rolling circle amplification (RCA) for 20 minutes according to the instructions of the BGI-SEQ500 sequencer, and subsequently sequenced on the sequencer via conventional PE50+10 strategy.

It should be noted that the blood cell-free DNA library obtained in the present disclosure can be sequenced through low-depth sequencing.

1.10 Sequencing Data Analysis 1.10.1 A Fastq file of sequencing data was subjected to quality filtering and alignment, after that a Bam file was obtained.

1.10.2 The full-length and position information of each fragment was obtained through pairing the double-ended fragments of the sequencing data.

Figure 4:
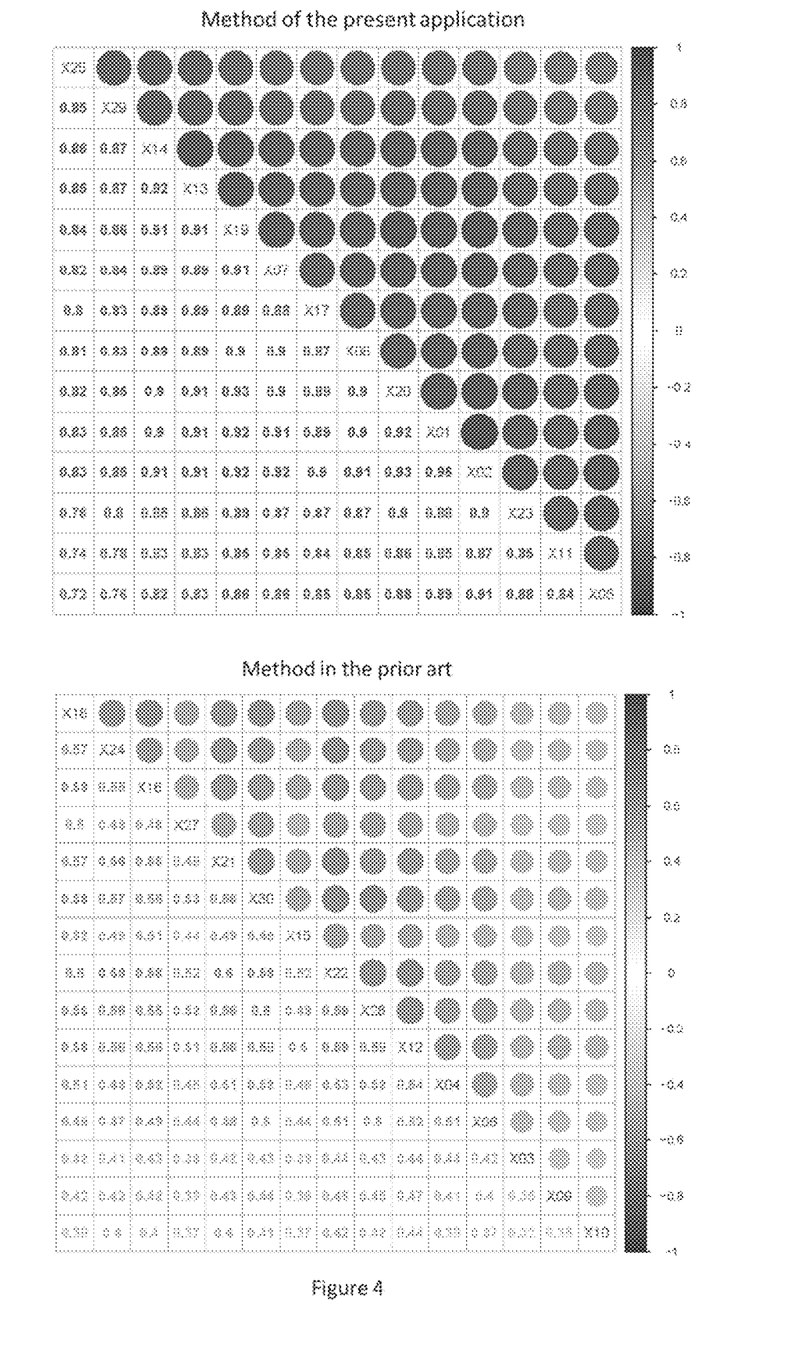
FIG. 4 is a graph showing the correlation between the data obtained by sample sequencing in Example 1.
Figure 5:
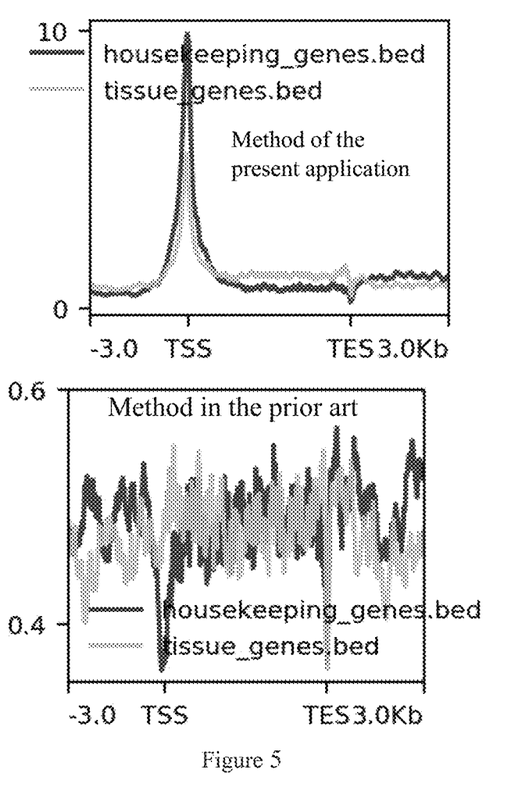
FIG. 5 is graphs showing the enrichment of transcription initiation regions of housekeeping gene and silent gene respectively among the fragments obtained after sequencing in Example 1.

1.10.3 Large fragments above 60 bp were screened out by filtering based on the fragment size. The correlation between the samples where the large fragments are derived, and the enrichment of these fragments in promoter and enhancer regions of different genes were calculated. The results are shown in FIGS. 4 and 5.

Figure 6:
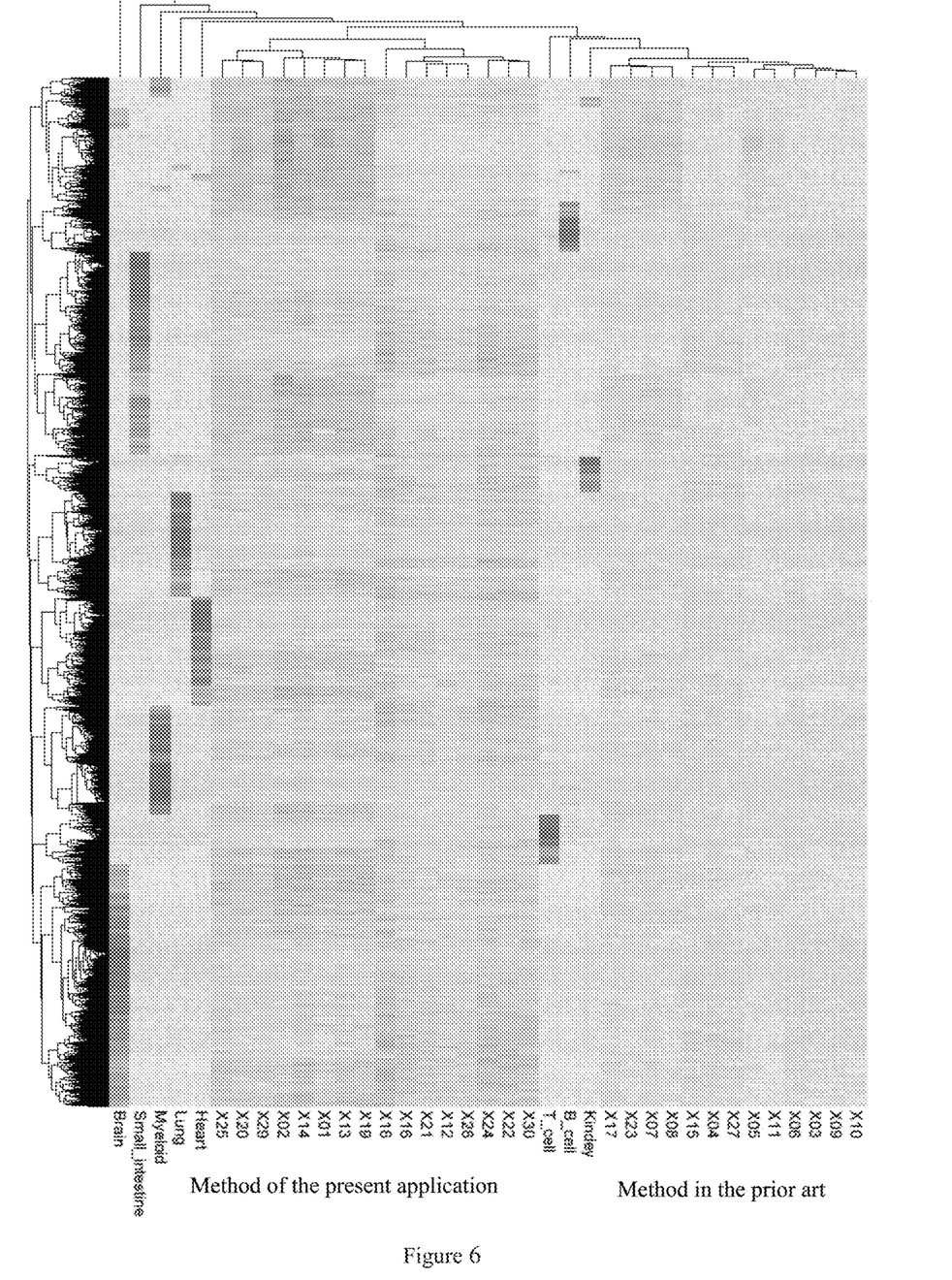
FIG. 6 is a graph showing clustering results of sample sequencing data and tissue sequencing data in Example 1.

1.10.4 These fragment data and the DNase-seq data of different human tissues from the ENCODE database were subjected to cluster analysis, and the results are shown in FIG. 6.

Comparative Example 1

In this comparative example, the prior art method was conducted as follows, that is, the cell-free DNAs in blood were extracted firstly before the transposition reaction.

2.1 Extraction of Blood Cell-Free DNAs Before Transposition Reaction 2.1.1 The blood cell-free DNAs were directly extracted from the purified plasma obtained in step 1.2 of Example 1, specifically referring to step 1.3 of Example 1.

2.1.2 Tn5 transposition reaction system was formulated on ice according to Table 8, mixed uniformly and subjected to transposition reaction at 37° C. on the constant temperature metal mixer for 30 minutes. During the transposition reaction, the Tn5 transposition reaction system was gently shaken for several times.

TABLE 8

Transposition reaction system for extracted blood cell-free DNAs

| Reagent | Volume (μL) |
| --- | --- |
| Extracted blood cell-free DNAs | 17 |
| 5×TAG buffer | 6 |
| Tn5 V5S | 1 |
| PBS | 6 |
| Total volume | 30 |

2.1.3 Termination Reaction 7.5 μL of 5× NT buffer was added, gently pipetted for 20 times and stayed at room temperature for 5 minutes.

2.1.4 Collection of DNAs by 1.8× Magnetic Beads 2.1.4.1 XP magnetic beads (AGENCOURT A63882) were taken out from the refrigerator at 4° C., mixed uniformly and placed at room temperature for 10 minutes.

2.1.4.2 1.8× XP magnetic beads were added into the tube in step 2.1.3, mixed uniformly by pipetting for 10 times, and stilled at room temperature for 5 minutes.

2.1.4.3 The tube was placed on the magnetic separator, stilled for 2 minutes, such that the magnetic beads were absorbed on the magnetic separator and the solution becomes clear.

2.1.4.4 The supernatant was removed while 5 μL of supernatant can be left to ensure no magnetic beads aspirated.

2.1.4.5 150 μL of 80% ethanol was added and stilled for 30 seconds, after that the supernatant was discarded.

2.1.4.6 The step 6.5 was repeated and the ethanol solution was maximally removed. The tube was dried in air until the magnetic beads are non-reflective.

2.1.4.7 The EP tube was taken out from the magnetic separator, 24 μL of nanofiltration (NF) water was added to dissolve DNAs, pipetted for 10 times to mix uniformly, stilled at room temperature for 3 minutes.

2.1.4.8 The EP tube was placed on the magnetic separator and stilled for 1 minute, after that the solution becomes clear.

2.1.4.9 The supernatant was transferred to a new EP tube.

2.1.4.10 Qubit dsDNA High sensitivity assay kit (INVITROGEN Q32854) was used for DNA quantification.

The DNA product obtained in step 2.1.4 of Comparative Example 1 was subsequently subjected to steps 1.4 to 1.10 of Example 1 to analyze the enrichment of large fragments above 60 bp from the library constructed in Comparative Example 1 in promoter and enhancer regions of different genes. The results are shown in FIG. 4.

As shown in FIG. 4, it can be clearly found that the correlation between samples obtained by the present method (Example 1) is significantly higher than the correlation between samples obtained by the prior art method (Comparative Example 1) after comparing and analyzing the results of Example 1 and Comparative Example 1.

As shown in FIG. 5, the present method (Example 1) exhibits a significantly increased region enrichment effect than the prior art method (Comparative Example 1).

As shown in FIG. 6, the fragment data obtained by the present method and the existing data of different human tissues can be clustered together according to cluster methods, indicating the present method is capable of capturing the cell-free DNA information from different human tissues, thus further for tissue traceability.

The applicant states that the detailed method of the present application is illustrated by the examples as described above, however the present application is not limited to this detailed method. That is, it does not mean that the present application has to rely on the detailed method to implement. Those skilled in the art should understand that any improvements to this application, the equivalent replacement of various raw materials of the product of this application, the addition of auxiliary components, the choice of specific means and the like all fall within the scope of protection and disclosure of this application.

What is claimed is:

1. A method for obtaining epigenetic information of an individual based on cell-free DNAs derived from nucleosome DNAs, comprising steps of:
   i) constructing a library of cell-free DNAs in a body fluid sample of an individual, which comprises:
      1) directly treating the body fluid sample using an enzyme, such that the cell-free DNAs in the body fluid sample are fragmented by the enzyme, wherein the nucleosome DNAs in cell-free DNAs of the body fluid sample are cut into fragments above 50 bp;
      2) amplifying the fragmented DNAs obtained in step 1) to obtain the library of cell-free DNAs in the body fluid sample; and
      3) subjecting the library of cell-free DNAs in the body fluid sample obtained in step 2) to cyclization and enzyme digestion, and
   ii) sequencing and analyzing the library of cell-free DNAs in the body fluid sample obtained in step i) to obtain epigenetic information of the individual,
   wherein analyzing the library of cell-free DNAs in the body fluid sample obtained in step i) comprises:
   obtaining full-length information of each of the fragmented DNAs; and
   distinguishing the nucleosome DNAs from naked DNAs in cell-free DNAs by filtering the fragmented DNAs of the sequencing data based on the full-length information of the fragmented DNAs, wherein the fragmented DNAs above 60 bp are screened out as the nucleosome DNAs and further analyzed to obtain epigenetic information of the individual,
   wherein the enzyme in step 1) is a transposase.

2. The method according to claim 1, wherein the transposase is Tn5 transposase.

3. The method according to claim 1, wherein the step 1) comprises utilizing the transposase to treat the body fluid sample containing the cell-free DNAs, such that the cell-free DNAs are fragmented and added with an adapter through a transposition reaction mediated by the transposase, thereby obtaining DNA fragments containing adapter sequences.

4. The method according to claim 3, wherein the adapter for the transposition reaction is an adapter mixture prepared by steps of:
   a) annealing a primer A of 5'-CTGTCTCTTATACA-CATCT-3' (SEQ ID NO: 1) and a primer B of 5'-TCGTCGGCAGCGTCAGATGTGTATAAGA-GACAG-3' (SEQ ID NO: 2) to obtain a first adapter, b) annealing a primer A of 5'-CTGTCTCTTATACA-CATCT-3' (SEQ ID NO: 1) and a primer C of 5'-GTCTCGTGGGCTCGGAGATGTGTATAAGA-GACAG-3' (SEQ ID NO: 3) to obtain a second adapter, and c) mixing the first adapter and the second adapter to obtain the adapter mixture.

5. The method according to claim 3, wherein the transposition reaction is conducted by incubating a transposase-embedding complex and the body fluid sample at a condition suitable for the transposition reaction.

6. The method according to claim 1, wherein the amplification in step 2) comprises two amplification processes; and the cycle number N to be used in a second amplification process is determined by a qPCR reaction after a first amplification process.

7. The method according to claim 3, wherein the step 1) further comprises extracting the DNA fragments containing adapter sequences in the body fluid sample.

8. The method according to claim 4, wherein the adapter mixture is embedded with the transposase to obtain a transposase-embedding complex for the transposition reaction.

9. The method according to claim 5, wherein the volume ratio of the transposase-embedding complex to the body fluid sample for the transposition reaction is 1:50 to 1:80.

10. The method according to claim 5, wherein the temperature for the transposition reaction is 35 to 40C.

11. The method according to claim 1, wherein the library of cell-free DNAs in the body fluid sample obtained in step 2) is a library comprising double-stranded DNAs, and the cyclization comprises denaturing the double-stranded DNAs in the library of cell-free DNAs in the body fluid sample into single-stranded DNAs, and ligating the single-stranded DNAs with the help of an oligonucleotide fragment which is complementary to a partial region of the single-stranded DNA through base-complementary pairing, to obtain a circular ligation product, wherein the enzyme digestion is performed by using exonuclease I and exonuclease III to remove non-cyclized DNAs.

12. The method according to claim 11, wherein the single-stranded DNAs are cyclized by using an oligonucleotide fragment of 5'-GCCATGTCGTTCTGTGAGC-CAAGG-3' (SEQ ID NO: 4).

13. The method according to claim 1, wherein analyzing the fragmented DNAs above 60 bp as the nucleosome DNAs to obtain epigenetic information of the individual further comprises:

calculating the enrichment of the fragmented DNAs above 60 bp in promoter and enhancer regions of genes.

14. The method according to claim 1, further comprising:

performing tissue traceability of the cell-free DNAs according to the epigenomic information of an individual.

* * * * *